(12) United States Patent
Yang et al.

(10) Patent No.: US 10,513,506 B2
(45) Date of Patent: Dec. 24, 2019

(54) 4-((6-(2-(2,4-DIFLUOROPHENYL)-1,1-DIFLUORO-2-HYDROXY-3-(1H-1,2,4-TRIAZOL-1-YL)PROPYL)PYRIDIN-3-YL AND PROCESSES OF PREPARATION

(71) Applicant: Dow AgroSciences LLC, Indianapolis, IN (US)

(72) Inventors: Qiang Yang, Zionsville, IN (US);
Daniel Knueppel, Zionsville, IN (US);
Michael T. Sullenberger, Westfield, IN (US);
Yan Hao, Zionsville, IN (US);
Sarah Ryan, Indianapolis, IN (US);
Jerod Patzner, Indianapolis, IN (US);
Gregory Whiteker, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/776,658

(22) PCT Filed: Nov. 17, 2016

(86) PCT No.: PCT/US2016/062447
§ 371 (c)(1),
(2) Date: May 16, 2018

(87) PCT Pub. No.: WO2017/087619
PCT Pub. Date: May 26, 2017

(65) Prior Publication Data
US 2018/0327380 A1 Nov. 15, 2018

Related U.S. Application Data

(60) Provisional application No. 62/256,486, filed on Nov. 17, 2015.

(51) Int. Cl.
*C07D 401/06* (2006.01)

(52) U.S. Cl.
CPC .................. *C07D 401/06* (2013.01)

(58) Field of Classification Search
None
See application file for complete search history.

(56) References Cited

U.S. PATENT DOCUMENTS

2014/0288107 A1 9/2014 Hoekstra et al.

FOREIGN PATENT DOCUMENTS

| CN | 103764647 A | 4/2014 | |
|---|---|---|---|
| WO | 200218339 A2 | 3/2002 | |
| WO | WO-2012177638 A1 * | 12/2012 | ........... C07D 401/14 |
| WO | 2014043376 A1 | 3/2014 | |
| WO | 2015143188 A1 | 9/2015 | |
| WO | 2016187201 | 11/2016 | |
| WO | 2017087643 | 5/2017 | |

OTHER PUBLICATIONS

International Searching Authority, International Search Report and Written Opinion for PCT/US2016/062447 dated Jan. 19, 2017, 5 pages.
Extended European Search Report for EP16867107.1, EPO, dated Mar. 19, 2019, 7 pages.

* cited by examiner

*Primary Examiner* — Zinna Northington Davis

(57) ABSTRACT

Provided herein is a process for the preparation of 4-((6-(2-(2,4-difluorophenyl)-1,1-difluoro-2-hydroxy-3-(1H-1,2,4-triazol-1-yl)propyl)pyridin-3-yl)oxy)benzonitrile.

28 Claims, No Drawings

4-((6-(2-(2,4-DIFLUOROPHENYL)-1,1-DIFLUORO-2-HYDROXY-3-(1H-1,2,4-TRIAZOL-1-YL)PROPYL)PYRIDIN-3-YL AND PROCESSES OF PREPARATION

CROSS-REFERENCE TO RELATED APPLICATIONS

This application is a national stage filing under 35 U.S.C. § 371 of International Application No. PCT/US2016/062447, filed Nov. 17, 2016, which claims priority to U.S. Provisional Application No. 62/256,486, filed Nov. 17, 2015, the entire contents of each of which is incorporated herein by reference.

FIELD

Provided herein is 4-((6-(2-(2,4-difluorophenyl)-1,1-difluoro-2-hydroxy-3-(1H-1,2,4-triazol-1-yl)propyl)pyridin-3-yl)oxy)benzonitrile and processes of preparation.

BACKGROUND

U.S. patent application Ser. Nos. 13/527,387, 13/527,426 and 13/528,283 describe inter alia certain metalloenzyme inhibitor compounds and their use as fungicides. The disclosure of each application is expressly incorporated by reference herein. Each of these patent applications describe various routes to generate metalloenzyme inhibiting fungicides. It may be advantageous to provide more direct and efficient methods for the preparation of metalloenzyme inhibiting fungicides and related compounds, e.g., by the use of reagents and/or chemical intermediates which provide improved time and cost efficiency.

SUMMARY OF THE DISCLOSURE

Provided herein is the compound 4-((6-(2-(2,4-difluorophenyl)-1,1-difluoro-2-hydroxy-3-(1H-1,2,4-triazol-1-yl)propyl)pyridin-3-yl)oxy)benzonitrile (I) and processes for its preparation. In one embodiment, provided herein, is a process for the preparation of the compound of the Formula I:

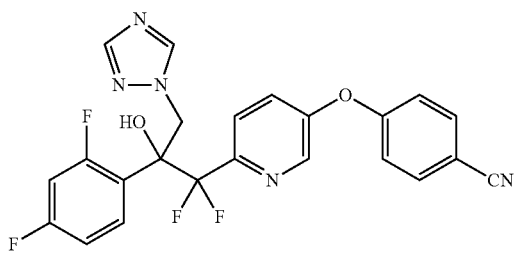

I which comprises contacting a compound of Formula II with 1H-1,2,4-triazole and a base.

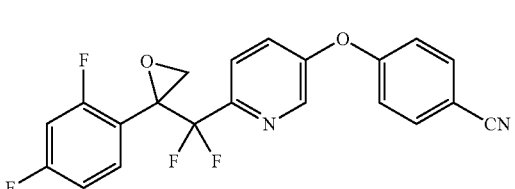

II

In another embodiment, the compound of Formula II may be prepared by contacting a compound of Formula III with a trialkylsulfoxonium halide and a base.

III

In another embodiment, the compound of Formula III may be prepared by contacting a compound of Formula IV

IV with a mixture formed by combining 1-bromo-2,4-difluorobenzene with a metal or an organometallic reagent, and an acid.

In another embodiment, the compound of Formula IV may be prepared by contacting a compound of Formula V with ethyl 2-bromo-2,2-difluoroacetate and a metal.

V

In another embodiment, the compound of Formula V may be prepared by contacting a compound of Formula VI with 4-fluorobenzonitrile or 4-nitrobenzonitrile, and a base.

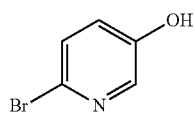 VI

In another embodiment, the compound of Formula VI may be prepared by contacting a compound of Formula VII with a magnesium-halogen exchange reagent, a borate, and an oxidizing agent.

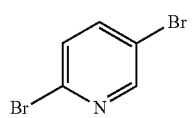 VII

The term "hydroxyl" refers to an —OH substituent.

The term "halogen" or "halo" refers to one or more halogen atoms, defined as F, Cl, Br, and I.

The term "organometallic" refers to an organic compound containing a metal, especially a compound in which a metal atom is bonded directly to a carbon atom.

Room temperature (RT) is defined herein as about 20° C. to about 25° C.

Throughout the disclosure, references to the compounds of Formula I and II are read as also including optical isomers and salts. Specifically, when compounds of Formula I and II contain a chiral carbon, it is understood that such compounds include optical isomers and racemates thereof. Exemplary salts may include: hydrochloride, hydrobromide, hydroiodide, and the like.

Certain compounds disclosed in this document can exist as one or more isomers. It will be appreciated by those skilled in the art that one isomer may be more active than the others. The structures disclosed in the present disclosure are drawn in only one geometric form for clarity, but are intended to represent all geometric and tautomeric forms of the molecule.

The embodiments described above are intended merely to be exemplary, and those skilled in the art will recognize, or will be able to ascertain using no more than routine experimentation, numerous equivalents of specific processes, materials and procedures. All such equivalents are considered to be within the scope of the invention and are encompassed by the appended claims.

DETAILED DESCRIPTION 4-((6-(2-(2,4-difluorophenyl)-1,1-difluoro-2-hydroxy-3-(1H-1,2,4-triazol-1-yl)propyl)pyridin-3-yl)oxy)benzonitrile (I) is provided herein and may be prepared from 2,5-dibromopyridine (VII) as shown in Examples 1-6.

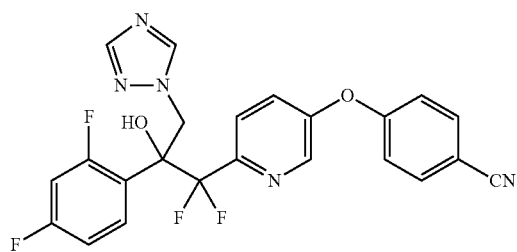

I

Example 1: Preparation of 6-bromopyridin-3-ol (VI)

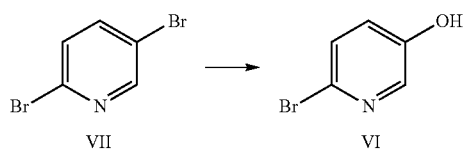

2,5-Dibromopyridine (VII) (9.98 g, 42.1 mmol) was dissolved in 53 mL anhydrous THF under nitrogen in a 250 mL 3-neck flask equipped with a mechanical stirrer, a thermocouple and a nitrogen inlet. A light tan solution was formed. A 2 M solution of i-PrMgCl in ether (23 mL) was added via syringe over 3 min. When approximately 50% of the Grignard solution had been added, a brown suspension formed. Addition of the Mg reagent caused an exotherm to 36° C. After stirring for 90 min, the suspension was cooled to 2° C., and neat trimethylborate (B(OMe)₃) was added rapidly via syringe. The reaction exothermed to 6° C., and the ice bath was removed. After stirring overnight, glacial acetic acid (3.79 g) was added, causing all solids to dissolve and a dark brown solution to form. The solution was cooled in an ice bath and 5.25 g of 30% hydrogen peroxide (an oxidizing agent) was added dropwise at a rate which kept the reaction temperature from exceeding 12° C. The reaction mixture was stirred for 90 min, and then diethyl ether (150 mL) and water (100 mL) were added. The aqueous layer was separated and extracted with ether (2×100 mL). The combined organics were washed with 100 mL 10% sodium bisulfite solution and then brine. The extracts were dried (MgSO₄) and rotary evaporated to a brown oil which formed a tan solid on standing (7.95 g). The crude product was adsorbed onto 15 g Celite® and purified by flash chromatography using a 220 g silica column and hexanes/EtOAc gradient. Fractions were evaporated to give 4.81 g (66% yield) of an off-white solid. NMR spectra were identical to that of an authentic sample of 6-bromo-3-pyridinol. $^1$H NMR (DMSO-d$_6$, 400 MHz) δ 10.24 (s, 1H), 7.94 (d, J=3.0 Hz, 1H), 7.42 (d, J=8.6 Hz, 1H), 7.17 (dd, J=3.0, 8.6 Hz, 1H); $^{13}$C NMR (DMSO-d$_6$, 101 MHz) δ 153.74, 138.13, 129.30, 128.14, 126.21.

The process exemplified in Example 1 may be conducted with additional Grignard reagents such as, for example, EtMgX, MeMgX, i-PrMgX, n-BuMgX, or PhMgX, wherein X is Cl or Br. The described process may also be conducted with a Grignard reagent, such as, for example, n-BuMgX, in the presence of a metal-halogen exchange reagent such as, for example, n-BuLi. The described process may also be conducted with alternative borates, such as, for example, B(OEt)₃ or B(Oi-Pr)₃. Solvents for use in this process may include those selected from THF, 2-MeTHF, MTBE, and dioxane.

The oxidizing agent used in the process exemplified in Example 1 may be selected from the group including hydrogen peroxide, peracetic acid, and a mixture of hydrogen peroxide and acetic acid.

Example 2: Preparation of 4-((6-bromopyridin-3-yl)oxy)benzonitrile (V)

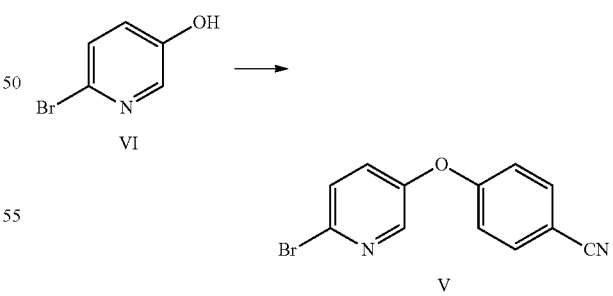

Method A:

To a 250-mL flask were charged 6-bromopyridin-3-ol (VI) (10 g, 57.5 mmol), 4-fluorobenzonitrile (8.35 g, 69.0 mmol), potassium carbonate (15.89 g, 115 mmol), and DMF (50 mL). The reaction was heated at 90° C. for 20 h, at which point HPLC analysis indicated that the reaction was complete. The reaction mixture was allowed to cool to 20° C., and then was further cooled to 0° C. Water (150 mL) was added, while maintaining the internal temperature at less than 15° C. (exotherm during the addition of water). The resulting suspension was stirred at 20° C. for 1 h and filtered. The filter cake was rinsed with water (2×25 mL) to afford a white solid. The solid was suspended in 95% ethanol (65 mL) and heated to 75° C. to afford a clear solution. It was allowed to cool to 20° C. over 1 h, and the resulting white suspension was stirred at 20° C. for 2 h. The suspension was filtered, and the solid was rinsed with 95% ethanol (2×10 mL). The solid was dried under vacuum to afford the desired product as a white solid (13.2 g, 83% yield). $^1$H NMR (400 MHz, CDCl$_3$) 8.22 (d, J=3.0 Hz, 1H), 7.73-7.63 (m, 2H), 7.53 (d, J=8.6 Hz, 1H), 7.33-7.23 (m, 1H), 7.14-7.00 (m, 2H); $^{13}$C NMR (101 MHz, CDCl$_3$) 160.13, 151.47, 142.54, 136.81, 134.47, 130.10, 129.12, 118.33, 118.23, 107.56; ESIMS: m/z 277.1 ([M+H]$^+$).

Method B:

To a 250-mL round bottom flask were charged 6-bromopyridin-3-ol (VI) (10 g, 57.5 mmol), 4-nitrobenzonitrile (8.94 g, 60.3 mmol), potassium carbonate (15.9 g, 114.9 mmol), and DMF (30 mL). The reaction was heated at 90° C. for 18 h, at which point HPLC analysis indicated that the reaction was complete. The reaction was allowed to cool to 20° C. and diluted with water (90 mL) at less than 50° C. The resulting suspension was stirred for 1 h and filtered. The filter cake was rinsed with water (2×50 mL) to give an off-white solid. The resulting solid was suspended in EtOH (40 mL) and heated to 75° C. to afford a clear solution. It was allowed to cool to 20° C. over 2 h, and stirred at this temperature for 1 h. The resulting suspension was filtered and the filter cake was rinsed with EtOH (2×10 mL). The filter cake was dried to afford the desired product as a white solid (12.9 g, 82% yield). mp: 116-119° C. $^1$H NMR (400 MHz, CDCl$_3$) δ 8.22 (d, J=3.0 Hz, 1H), 7.67 (d, J=8.8 Hz, 2H), 7.53 (d, J=8.6 Hz, 1H), 7.29 (dd, J=8.7, 2.9 Hz, 1H), 7.07 (d, J=8.8 Hz, 2H). $^{13}$C NMR (101 MHz, CDCl$_3$) δ 160.13, 151.47, 142.55, 136.81, 134.48, 130.13, 129.13, 118.34, 107.55. ESIMS: m/z 277.0 ([M+H]$^+$).

The process exemplified in Example 2 may be conducted in a solvent selected from one or more of dimethyl sulfoxide (DMSO), dimethylacetamide (DMA), dimethylformamide (DMF), and N-methyl-2-pyrrolidone (NMP). Bases for use in this process may include metal carbonates such as potassium carbonate and cesium carbonate, metal hydrides such as NaH, metal hydroxides such as NaOH and KOH, and metal bicarbonates.

The process exemplified in Example 2 may be conducted between about room temperature and about 120° C.

Example 3: Preparation of ethyl 2-(5-(4-cyanophenoxy)pyridin-2-yl)-2,2-difluoroacetate (IV)

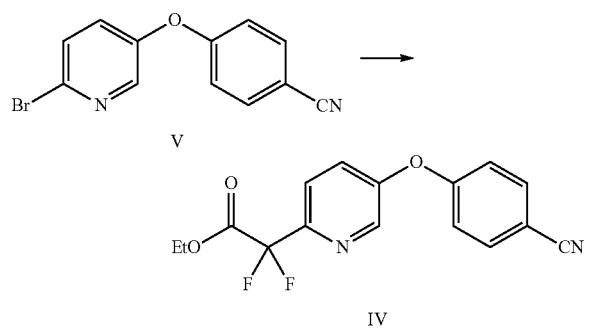

Method A:

Ethyl 2-bromo-2,2-difluoroacetate (12.27 mL, 94 mmol) and copper powder (14-25 μm, 9.60 g, 151 mmol) were added to a solution of 4-((6-bromopyridin-3-yl)oxy)benzonitrile (V) (20 g, 72.0 mmol) in DMF (140 mL) under nitrogen. The resulting brown suspension was heated at 60° C. under nitrogen for 18 h, at which point HPLC analysis indicated that the reaction was complete. The mixture was cooled to 20° C., and MTBE (280 mL) was added. The resulting mixture was stirred for 10 min and filtered through a Celite® pad. The Celite® pad was rinsed with MTBE (2×140 mL). The filtrate was washed with sat. NH$_4$Cl (200 mL), brine (3×140 mL), and water (2×140 mL). The organic layer was dried over anhydrous Na$_2$SO$_4$, filtered, and concentrated to afford the crude product as a light brown oil (21 g, 92%) in purity sufficient for use in the next step directly. This crude product was further purified by column chromatography (10-20% EtOAc/hexanes) to give the desired product as a white solid (16 g, 70% yield); mp 45-48° C. $^1$H NMR (400 MHz, CDCl$_3$) δ 8.44 (d, J=2.7 Hz, 1H), 7.79 (dd, J=8.6, 0.7 Hz, 1H), 7.73-7.66 (m, 2H), 7.49 (dd, J=8.6, 2.7 Hz, 1H), 7.14-7.08 (m, 2H), 4.40 (q, J=7.1 Hz, 2H), 1.36 (t, J=7.1 Hz, 3H); ESIMS m/z 319.1 ([M+H]$^+$).

Method B:

To a 15 L jacketed reactor was added 4-((6-bromopyridin-3-yl)oxy)benzonitrile (900 g, 3173 mmol), ethyl 2-bromo-2,2-difluoroacetate (541 mL, 4125 mmol), copper (423 g, 6664 mmol), and DMSO (4500 mL) under nitrogen to give a brown suspension. The reaction was heated at 40° C. for 8 h, at which point HPLC analysis indicated that the reaction was complete. It was allowed to cool to 20° C. and MTBE (4000 mL) was added. The mixture was stirred for 30 minutes and filtered through a Celite® pad. The filter pad was rinsed with MTBE (2×1000 mL) and the combined filtrates were rinsed with brine (3×2000 mL). The first aqueous layer was extracted with MTBE (2×1000 mL). The combined organic layers were washed with a saturated NH$_4$Cl solution (2×2000 mL) and brine (3×2000 mL), and concentrated to give the desired product as a brown oil (1030 g, 96% yield). $^1$H NMR (400 MHz, CDCl$_3$) δ 8.44 (d, J=2.7 Hz, 1H), 7.79 (dd, J=8.6, 0.7 Hz, 1H), 7.73-7.66 (m, 2H), 7.49 (dd, J=8.6, 2.7 Hz, 1H), 7.14-7.08 (m, 2H), 4.40 (q, J=7.1 Hz, 2H), 1.36 (t, J=7.1 Hz, 3H).

The process exemplified in Example 3 may be conducted in a solvent selected from one or more of DMSO, DMF, THF, and NMP, and with a metal such as copper.

The process exemplified in Example 3 may be conducted between about room temperature and about 100° C.

Example 4: Preparation of 4-((6-(2-(2,4-difluorophenyl)-1,1-difluoro-2-oxoethyl)pyridin-3-yl)oxy)benzonitrile (III)

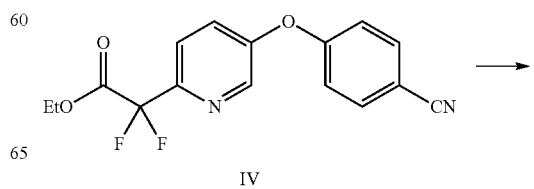

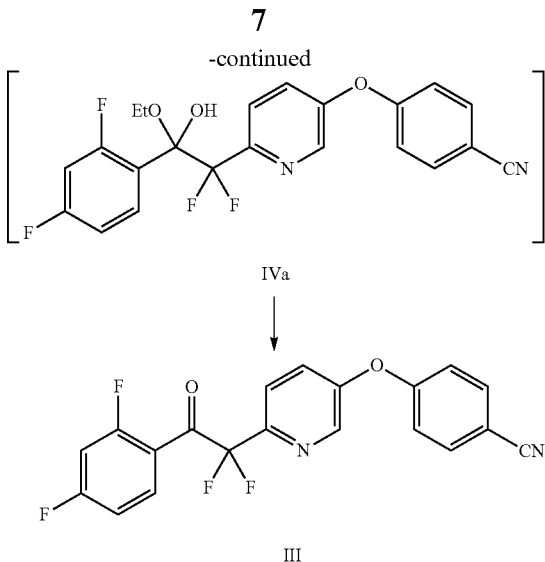

Method A:

A suspension of Mg turnings (3.47 g, 143 mmol) in THF (250 mL) was heated to 35° C. under nitrogen. A portion of 1-bromo-2,4-difluorobenzene (1 mL, 8.85 mmol) was added to the reactor, and the resulting mixture was heated at 35° C. for 30 min to initiate the reaction. The reaction mixture was cooled to 30° C., and the remainder of 1-bromo-2,4-difluorobenzene (16.4 mL, 145.15 mmol) was added to the reactor at 28-32° C. over 30 min. The reaction was stirred at 30° C. for 2 h, at which point complete consumption of Mg was observed. The reaction was cooled to less than 0° C., and a solution of ethyl 2-(5-(4-cyanophenoxy)pyridin-2-yl)-2,2-difluoroacetate (IV) (35 g, 110 mmol) in THF (100 mL) was added at less than 5° C. over 30 min. The reaction was stirred at 0° C. for 1 h and quenched into a 2 N HCl solution (150 mL) at less than 10° C. (pH=1-2). The reaction was stirred at 20° C. for 18 h, at which point HPLC analysis indicated that there was still about 10% of the hemiketal intermediate of Formula IVa remaining. It was further stirred at 30° C. for 5 h, at which point HPLC analysis indicated that the hemiketal intermediate was fully consumed. The layers were separated, and the aqueous layer was extracted with EtOAc (100 mL). The combined organic layers was washed with a sat. NaHCO$_3$ solution (100 mL), dried over anhydrous Na$_2$SO$_4$, filtered, and concentrated to give a light tan solid (45.6 g). The solid was dissolved in EtOAc (60 mL) at 60° C., and heptane (100 mL) was added. The mixture was seeded and stirred at 20° C. for 18 h to afford a suspension. The suspension was filtered and the solid was dried to afford the desired product as a white solid (25.5 g). The filtrate was concentrated and recrystallized from MTBE (50 mL) and heptane (100 mL) to give a light brown solid (14.1 g) after drying, affording a combined yield of 90%. $^1$H NMR (400 MHz, CDCl$_3$) δ 8.37 (d, J=2.7 Hz, 1H), 8.08 (td, J=8.4, 6.4 Hz, 1H), 7.87 (d, J=8.6 Hz, 1H), 7.75-7.66 (m, 2H), 7.54 (dd, J=8.6, 2.8 Hz, 1H), 7.17-7.08 (m, 2H), 7.01 (dddd, J=8.6, 7.6, 2.5, 0.9 Hz, 1H), 6.84 (ddd, J=11.0, 8.6, 2.4 Hz, 1H); ESIMS m/z 387.0 ([M+H]$^+$).

Method B:

A suspension of Mg turnings (107 g, 4.3 mol) in THF (6000 mL) was heated to 35° C. under nitrogen. A portion of 1-bromo-2,4-difluorobenzene (32 mL, 0.28 mol) was added to the reactor at 35° C., and the resulting mixture was heated at 35° C. for 30 min to initiate the reaction. The reaction mixture was cooled to 15° C., and the remainder of 1-bromo-2,4-difluorobenzene (500 mL, 4.45 mol) was added to the reactor at 15-20° C. over 80 min. The reaction was stirred at 20° C. for 1 h and cooled to −20° C. A solution of ethyl 2-(5-(4-cyanophenoxy)pyridin-2-yl)-2,2-difluoroacetate (IV) (1052 g, 3.07 mol) in THF (100 mL) was added at less than −5° C. over 40 min. The container and addition funnel were rinsed with THF (200 mL) and the rinse solvent was added to the reaction. The reaction was stirred at −20° C. for 2 h and quenched into a 4 N HCl solution (1500 mL) at less than 10° C. The reaction was allowed to warm to 20° C. and stirred for 16 h, at which point HPLC analysis indicated that the reaction was complete. The layers were separated, and the aqueous layer was extracted with MTBE (3×400 mL). The combined organic layers were washed with a saturated NaHCO$_3$ solution (2×1000 mL), brine (2×1000 mL), and water (1000 mL). The organic layer was dried, filtered, and concentrated to afford a brown solid (1264 g). The resulting solid was suspended in 3:1 heptane/MTBE (1000 mL) and heated at 60° C. for 1 h. The resulting suspension was cooled to ambient temperature and filtered. The solid was suspended in 3:1 heptane/MTBE (1000 mL) and heated at 60° C. for 1 h. The resulting suspension was cooled to ambient temperature and filtered to give the desired product as a tan solid after drying (1080 g, 86% yield). Analysis of the isolated product was in agreement with that of the previously obtained sample.

The process exemplified in Example 4 may be conducted in a solvent that is an aprotic solvent selected from one or more of diethyl ether, tetrahydrofuran (THF), 1,2-dimethoxyethane (DME), toluene, dioxane and methyl t-butyl ether (MTBE).

The process exemplified in Example 4 may be conducted with an organometallic reagent that is either an aryl Grignard or an aryl lithium reagent formed by a reaction of 2,4-difluoro-1-bromobenzene with one of magnesium, an alkyl-lithium reagent such as n-butyllithium, or a Grignard reagent such as isopropylmagnesium chloride.

The process exemplified in Example 4 may be conducted between about −80° C. and about 50° C.

The hemiketal of Formula IVa may be isolated as an intermediate in the process to prepare the compound of Formula III under certain reaction conditions. Addition of an acid to a reaction mixture containing the hemiketal of Formula IVa may result in conversion of it into the desired product of Formula III.

Suitable acids for use in the process exemplified in Example 4 may be selected from the group including HCl, HBr, H$_2$SO$_4$, H$_3$PO$_4$, HNO$_3$, acetic acid and trifluoroacetic acid.

Example 5: Preparation of 4-((6-((2-(2,4-difluorophenyl)oxiran-2-yl)difluoromethyl)pyridin-3-yl)oxy)benzonitrile (II)

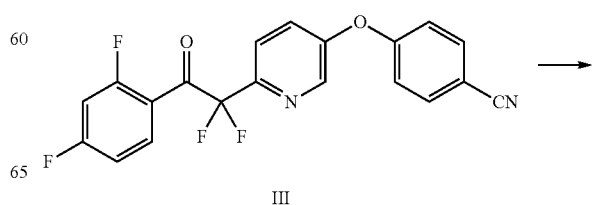

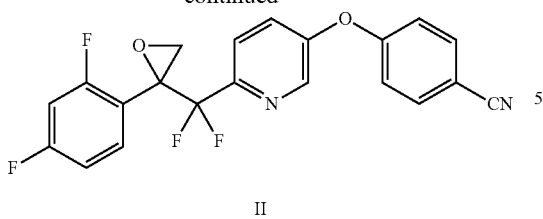

II

To a three neck, 3000 mL round bottom flask equipped with an overhead stirrer, a nitrogen inlet and a thermocouple were added trimethylsulfoxonium iodide (46.4 g, 211 mmol), anhydrous DMSO (270 mL), and THF (270 mL). NaH (7.13 g, 178 mmol) was added in portions under nitrogen, while maintaining internal temperature below 20° C. The reaction mixture was stirred at 20° C. for 1 h. 4-((6-(2-(2,4-Difluorophenyl)-1,1-difluoro-2-oxoethyl)pyridin-3-yl)oxy)benzonitrile (III) (65.9 g, 162 mmol) in THF (270 ml) was added slowly to maintain the temperature between −10° C. and 0° C. The reaction was stirred at between −5° C. and 0° C. for 40 min, at which point LCMS indicated complete conversion to product. The reaction mixture was diluted with EtOAc (1000 mL). Saturated NaHCO$_3$ (30 mL) was slowly added to quench the reaction. Brine (300 mL) was added, and the mixture was extracted with EtOAc. The layers were separated and the aqueous layer was extracted with EtOAc (2×150 mL). The combined organic phases were washed with brine (2×) and water (1×). The organics were dried over anhydrous Na$_2$SO$_4$, and concentrated to give the crude product as an amber gum (72 g, 87% purity, 97% corrected yield). This crude product was used directly in the next step. A small sample of this crude product (2.2 g) was purified by column chromatography (eluent: 0-20% EtOAc/hexanes) to obtain an analytical sample as a white solid: mp 110-113° C. $^1$H NMR (500 MHz, CDCl$_3$) δ 8.47 (d, J=2.7 Hz, 1H), 7.74-7.63 (m, 2H), 7.53 (dd, J=8.6, 0.7 Hz, 1H), 7.48-7.36 (m, 2H), 7.13-7.03 (m, 2H), 6.90-6.83 (m, 1H), 6.75 (ddd, J=9.9, 8.8, 2.5 Hz, 1H), 3.46 (d, J=5.1 Hz, 1H), 2.99 (dt, J=4.7, 2.0 Hz, 1H); $^{13}$C NMR (126 MHz, CDCl$_3$) δ 164.49 (d, J=11.8 Hz), 162.40 (dd, J=24.7, 12.0 Hz), 160.29 (d, J=12.2 Hz), 159.67, 153.00, 147.70 (t, J=28.8 Hz), 141.50, 134.54132.57 (dd, J=10.0, 4.7 Hz), 126.90, 122.96 (t, J=4.3 Hz), 118.85, 118.22, 117.31 (t, J=249.5 Hz), 116.99 (dd, J=14.9, 3.8 Hz), 111.40 (dd, J=21.7, 3.6 Hz), 107.90, 103.87 (t, J=25.3 Hz), 57.33 (t, J=34.1 Hz), 50.10 (d, J=3.9 Hz).

The process exemplified in Example 5 may be conducted with a trialkylsulfoxonium halide selected from one of trimethylsulfoxonium iodide, trimethylsulfoxonium bromide and trimethylsulfoxonium chloride. The process includes a base that may be selected from the group including sodium hydride, potassium carbonate, cesium carbonate, and sodium tert-butoxide, and a solvent selected from at least one of DMSO, DMF, THF, and NMP.

The process exemplified in Example 5 may be conducted between about −20° C. and about 100° C.

Example 6: Preparation of 4-((6-(2-(2,4-difluorophenyl)-1,1-difluoro-2-hydroxy-3-(1H-1,2,4-triazol-1-yl)propyl)pyridin-3-yl)oxy)benzonitrile (I)

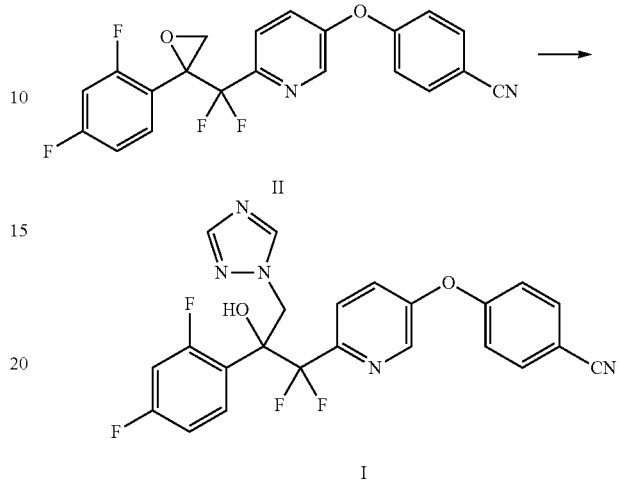

To a magnetically stirred mixture of 4-((6-((2-(2,4-difluorophenyl)oxiran-2-yl)difluoromethyl)pyridin-3-yl)oxy)benzonitrile (II) (10.2 g, 20.64 mmol) in anhydrous DMSO (103 mL) were added 1H-1,2,4-triazole (4.36 g, 61.9 mmol) and K$_2$CO$_3$ (14.26 g, 103 mmol) under nitrogen. The reaction mixture was stirred at 55° C. for 16 h, and cooled to ambient temperature. The reaction mixture was poured into ice/water (200 mL) to give an off-white suspension. The suspension was filtered, and the crude solid was purified by column chromatography (330 g silica, 80% EtOAc/hexanes) to afford the desired product as an off-white resin (8.3 g, 83% yield). $^1$H NMR (400 MHz, CDCl3) δ 8.36 (d, J=2.6 Hz, 1H), 8.15 (s, 1H), 7.78-7.67 (m, 3H), 7.58 (d, J=8.7 Hz, 1H), 7.51-7.36 (m, 2H), 7.14-7.04 (m, 2H), 6.79-6.68 (m, 2H), 6.29 (s, 1H), 5.40 (d, J=14.4 Hz, 1H), 4.88 (dd, J=14.4, 1.6 Hz, 1H); ESIMS m/z 470.0 ([M+H]$^+$).

The process exemplified in Example 6 may be conducted with a base selected from one of potassium carbonate, cesium carbonate, and sodium t-butoxide.

The process exemplified in Example 6 may be conducted in a solvent selected from at least one of dimethylsulfoxide, dimethylformamide, tetrahydrofuran, and N-methyl-2-pyrrolidone, and at a temperature between about room temperature and about 100° C.

What is claimed is:
1. A method of making a compound of Formula I

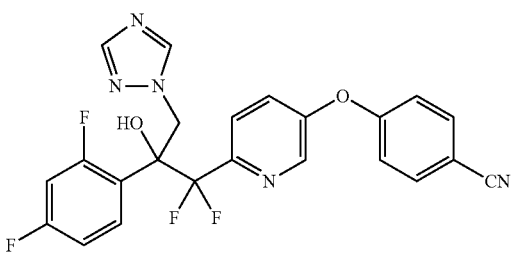

I comprising the steps of:
contacting a compound of Formula III

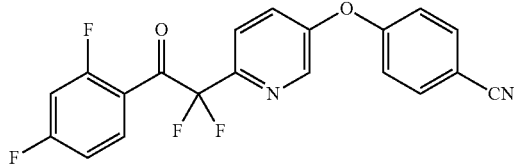

with a trialkylsulfoxonium halide and a base to prepare the compound of Formula II, and
contacting a compound of Formula II

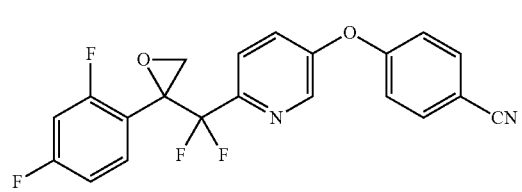

with 1H-1,2,4-triazole and a base.

2. The method of claim 1, wherein the base is one of potassium carbonate, cesium carbonate, and sodium t-butoxide.

3. The method of claim further comprising a solvent selected from the group including dimethylsulfoxide, dimethylformamide, sulfolane, tetrahydrofuran, water, N-methyl-2-pyrrolidone, and mixtures thereof.

4. The method of claim 1, wherein the contacting the compound of Formula II is carried out between about room temperature and about 100° C.

5. The method of claim 1, wherein the trialkylsulfoxonium halide is one of trimethylsulfoxonium iodide, trimethylsulfoxonium bromide and trimethylsulfoxonium chloride.

6. The method of claim 1, wherein the base is selected from the group including sodium hydride, potassium carbonate, cesium carbonate, and sodium tert-butoxide.

7. The method of claim 1, further comprising a solvent selected from the group including DMSO, DMF, THF, water, NMP, and mixtures thereof.

8. The method of claim 1, wherein the contacting the compound of Formula III is carried out between about −20° C. and about 100° C.

9. The method of claim 1, further comprising the step of:
contacting a compound of Formula IV

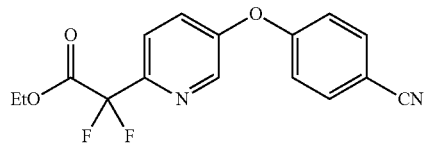

with a mixture formed by combining 1-bromo-2,4-difluorobenzene with a metal or an organometallic reagent, and an acid,
to prepare the compound of Formula III.

10. The method of claim 9, further comprising an aprotic solvent i-s selected from the group including diethyl ether, tetrahydrofuran, 1,2-dimethoxyethane, toluene, dioxane, methyl t-butyl ether, and mixtures thereof.

11. The method of claim 9, wherein the metal is magnesium and the organometallic reagent is an alkyllithium or an alkylmagnesium halide.

12. The method of claim 11, wherein the alkyllithium is n-butyllithium, and the alkylmagnesium halide is isopropylmagnesium chloride.

13. The method of claim 9, wherein the contacting is carried out between about −80° C. and about 50° C.

14. The method of claim 9, wherein the acid is selected from the group including HCl, HBr, $H_2SO_4$, $H_3PO_4$, $HNO_3$, acetic acid, and trifluoroacetic acid.

15. The method of claim 9, further comprising the step of:
contacting a compound of Formula V

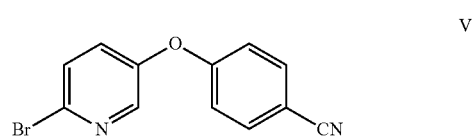 [SMILES: N#Cc1ccc(Oc2ccc(Br)nc2)cc1]

with ethyl 2-bromo-2,2-difluoroacetate and a metal to prepare the compound of Formula IV.

16. The method of claim 15, wherein the metal is copper.

17. The method of claim 15, further comprising a solvent selected from the group including DMSO, DMF, THF, NMP, and mixtures thereof.

18. The method of claim 15, wherein the contacting is carried out between about room temperature and about 100° C.

19. The method of claim 15, further comprising the step of:
contacting a compound of Formula VI

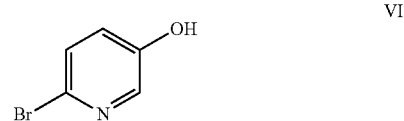

with 4-fluorobenzonitrile or 4-nitrobenzonitrile, and a base to prepare the compound of Formula V.

20. The method of claim 19, wherein the base is selected from cesium carbonate and potassium carbonate.

21. The method of claim 19, wherein the step of contacting the compound of Formula VI with 4-fluorobenzonitrile or 4-nitrobenzonitrile, and a base, further includes a solvent.

22. The method of claim 21, wherein the solvent is selected from the group including dimethyl sulfoxide, N,N-dimethylacetamide, N,N-dimethylformamide, N-methyl-2-pyrrolidone, and mixtures thereof.

23. The method of claim 19, wherein the step of contacting the compound of Formula VI with 4-fluorobenzonitrile or 4-nitrobenzonitrile, and a base is carried out between about room temperature and about 120° C.

24. The method of claim 19, further comprising the step of:
contacting a compound of Formula VII

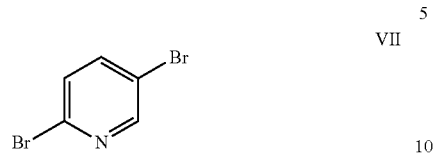

VII with a magnesium-halogen exchange reagent, a borate, and an oxidizing agent to prepare the compound of Formula VI.

25. The method of claim 24, wherein the magnesium-halogen exchange reagent is iso-propylmagnesium chloride.

26. The method of claim 24, wherein the borate is selected from the group including $B(OMe)_3$, $B(OEt)_3$ and $B(Oi-Pr)_3$.

27. The method of claim 24, wherein the oxidizing agent is selected from the group including hydrogen peroxide, peracetic acid, and a mixture of hydrogen peroxide and acetic acid.

28. The method of claim 24, further comprising a solvent selected from the group including THF, 2-methyltetrahydrofuran, methyl t-butyl ether, dioxane, and mixtures thereof.

* * * * *